US009824876B2

(12) United States Patent
Mannino et al.

(10) Patent No.: US 9,824,876 B2
(45) Date of Patent: Nov. 21, 2017

(54) FLUID CHROMATOGRAPHY INJECTORS AND INJECTOR INSERTS

(75) Inventors: Rosario Mannino, North Haven, CT (US); William Goodman, Waterbury, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 882 days.

(21) Appl. No.: 13/035,316

(22) Filed: Feb. 25, 2011

(65) Prior Publication Data
US 2011/0211992 A1 Sep. 1, 2011

Related U.S. Application Data

(60) Provisional application No. 61/308,461, filed on Feb. 26, 2010.

(51) Int. Cl.
*G01N 30/02* (2006.01)
*G01N 30/16* (2006.01)
*H01J 49/24* (2006.01)
*H01J 49/00* (2006.01)
G01N 30/24 (2006.01)
G01N 30/60 (2006.01)

(52) U.S. Cl.
CPC .............. *H01J 49/24* (2013.01); *G01N 30/16* (2013.01); *H01J 49/005* (2013.01); *G01N 30/24* (2013.01); *G01N 30/6026* (2013.01)

(58) Field of Classification Search
CPC .................................................... G01N 30/16
USPC ...... 422/70, 89, 544–546; 96/105; 73/23.35, 73/23.39, 23.41, 61.52, 61.55, 61.56; 210/198.2
See application file for complete search history.

(56) References Cited

U.S. PATENT DOCUMENTS

| 3,471,261 | A | * | 10/1969 | Patterson ...................... 436/161 |
| 4,045,343 | A | * | 8/1977 | Achener et al. .............. 210/101 |
| 5,123,276 | A | * | 6/1992 | Hartman et al. .............. 73/23.41 |
| 5,811,665 | A | | 9/1998 | Gregor |
| 6,662,626 | B2 | | 12/2003 | Van Der Maas |
| 6,666,074 | B2 | | 12/2003 | Gerner |
| 6,783,673 | B2 | * | 8/2004 | Horsman et al. .......... 210/198.2 |
| 6,907,796 | B2 | | 6/2005 | Bremer |
| 7,384,457 | B2 | | 6/2008 | Emmons |
| 2002/0185441 | A1 | | 12/2002 | Gjerde |
| 2004/0035774 | A1 | | 2/2004 | Horsman |
| 2004/0236083 | A1 | | 11/2004 | Libert |

(Continued)

FOREIGN PATENT DOCUMENTS

GB      10742416      6/1967
WO      2009154984      12/2009

OTHER PUBLICATIONS

ISR/WO for PCT/US2011/026241 dated Apr. 26, 2011.
ISR/WO for PCT/US2011/026385 dated May 2, 2011.
Extended European Search Report for EP11748146.5.

*Primary Examiner* — Jan Ludlow
(74) *Attorney, Agent, or Firm* — Rhodes IP PLC; Christopher R Rhodes

(57) ABSTRACT

Certain embodiments described herein are directed to injector inserts and injector assemblies. In some examples, an injector insert that includes an inlet comprising a substantially inert metal is described. In other examples, an injector that includes a major amount of a substantially inert metal in a fluid flow path is disclosed. Devices and systems using the injectors inserts and injectors are also described.

20 Claims, 9 Drawing Sheets

(56) References Cited

U.S. PATENT DOCUMENTS

2007/0181479 A1 8/2007 Yamamoto
2007/0283746 A1 12/2007 Gerhardt

* cited by examiner

| Phenols Linearity Testing | | R squared | Response at 0.5 ppm | Response at 1 ppm |
|---|---|---|---|---|
| Standard | ring | 0.9764 | N/A | 1850 |
| Stainless | no ring | 0.9854 | N/A | 2287 |
| Gold | ring | 0.9853 | 540 | 9927 |
| Titanium | no ring | 0.9891 | | |
| | ring | 0.9748 | 5626 | 22662 |
| Polished Ti | ring | 0.9888 | 1251 | 6717 |
| | no ring | 0.9959 | 2458 | 8739 |

FIG. 11

FLUID CHROMATOGRAPHY INJECTORS AND INJECTOR INSERTS

PRIORITY APPLICATION

This application claims priority to, and the benefit of, U.S. Provisional Application No. 61/308,461 filed on Feb. 26, 2010, the entire disclosure of which is hereby incorporated herein by reference for all purposes.

RELATED APPLICATION

This application is related to commonly owned provisional application filed on Feb. 26, 2010 and having U.S. Application No. 61/308,499 and entitled "JET ASSEMBLY FOR USE IN DETECTORS AND OTHER DEVICES," the entire disclosure of which is hereby incorporated herein by reference for all purposes.

TECHNOLOGICAL FIELD

Certain embodiments described herein are directed to fluid injectors and fluid injector inserts configured for use with fluid chromatography devices such as, for example, a gas chromatography system.

BACKGROUND

Most chromatography systems include an injector assembly that permits introduction of a sample into the system. The materials commonly used in the injector assemblies can react with the sample and reduce the accuracy of the measurements.

SUMMARY

In one aspect, a fluid injector insert comprising an inlet and an outlet, in which the insert is constructed and arranged to couple to an injector assembly to fluidically couple the inlet of the insert to a fluid flow path of the injector assembly, in which the inlet of the insert comprises a substantially inert metal material is provided.

In certain examples, the substantially inert metal material is present in a major amount. In other examples, the substantially inert metal material comprises titanium, aluminum, yttrium or combinations thereof. In additional examples, the substantially inert metal material comprises titanium oxide, aluminum oxide, yttrium oxide or combinations thereof. In further examples, the substantially inert metal material comprises nickel. In some examples, the substantially inert metal material can be a Hastelloy® alloy. In certain examples, the substantially inert metal material comprises chromium. In other examples, the substantially inert metal material can be an Inconel® alloy. In additional examples, the inlet and the outlet each comprises a substantially inert metal material. In some examples, the substantially inert metal material of the inlet and the outlet are the same material.

In another aspect, a fluid injector insert comprising an inlet and an outlet, in which the insert is constructed and arranged to couple to an injector assembly to fluidically couple the inlet to a fluid flow path of the injector assembly, in which the inlet of the insert comprises a non-catalytic metal material present in an effective amount to deter catalysis by the inlet is disclosed.

In certain embodiments, the non-catalytic metal material is present in a major amount. In other embodiments, the non-catalytic metal material comprises titanium, aluminum, yttrium or combinations thereof. In further embodiments, the non-catalytic metal material comprises titanium oxide, aluminum oxide, yttrium oxide or combinations thereof. In additional embodiments, the non-catalytic metal material comprises nickel. In some embodiments, the non-catalytic metal material can be a Hastelloy® alloy. In some embodiments, the non-catalytic metal material comprises chromium. In additional embodiments, the non-catalytic metal material can be an Inconel® alloy. In further embodiments, the inlet and the outlet each comprises a non-catalytic metal material. In some embodiments, the non-catalytic metal material of the inlet and the outlet are the same material.

In an additional aspect, a fluid injector comprising an inlet and an outlet, the fluid injector further comprising a fluid flow path fluidically coupled to the inlet, in which the inlet and the outlet are configured to receive a chromatography column, and in which the inlet comprises a non-catalytic metal material present in an major amount to deter catalysis by the inlet is described.

In certain examples, the non-catalytic metal material comprises titanium, aluminum, yttrium or combinations thereof. In other examples, the non-catalytic metal material comprises titanium oxide, aluminum oxide, yttrium oxide or combinations thereof. In additional examples, the non-catalytic metal material comprises nickel. In further examples, the non-catalytic metal material can be a Hastelloy® alloy. In some examples, the non-catalytic metal material comprises chromium. In other examples, the non-catalytic metal material can be an Inconel® alloy. In additional examples, the inlet and the outlet each comprises a non-catalytic metal material present in an effective amount to deter catalysis. In some examples, the non-catalytic material of the inlet and the outlet are the same material. In other examples, the non-catalytic material of the inlet and the outlet are a different material.

In another aspect, a fluid injector comprising an inlet and an outlet, the fluid injector further comprising a fluid flow path fluidically coupled to the inlet, in which the inlet and the outlet are configured to receive a chromatography column, and in which the inlet comprises a major amount of a substantially inert metal material is provided.

In certain embodiments, the substantially inert metal material comprises titanium, aluminum, yttrium or combinations thereof. In some embodiments, the substantially inert metal material comprises titanium oxide, aluminum oxide, yttrium oxide or combinations thereof. In other embodiments, the substantially inert metal material comprises nickel. In additional embodiments, the substantially inert metal material can be a Hastelloy® alloy. In other embodiments, the substantially inert metal material comprises chromium. In further embodiments, the substantially inert metal material can be an Inconel® alloy. In additional embodiments, the inlet and the outlet each comprises a major amount of a substantially inert metal material. In other embodiments, the substantially inert metal material of the inlet and the outlet are the same material. In some embodiments, the substantially inert metal material of the inlet and the outlet are a different material.

In an additional aspect, a fluid injector insert comprising an inlet and an outlet, in which the inlet comprises a non-catalytic, non-glass material present in an effective amount to deter catalysis by the inlet is disclosed.

In certain examples, the non-catalytic, non-glass material comprises titanium, aluminum, yttrium or combinations thereof. In some examples, the non-catalytic, non-glass material comprises titanium oxide, aluminum oxide, yttrium oxide or combinations thereof. In other examples, the non-catalytic, non-glass material comprises nickel. In additional examples, the non-catalytic, non-glass material can be a Hastelloy® alloy. In further examples, the non-catalytic, non-glass material comprises chromium. In some examples, the non-catalytic, non-glass material can be an Inconel® alloy. In certain examples, the inlet and the outlet each comprises a non-catalytic, non-glass material present in an effective amount to deter catalysis. In some examples, the non-catalytic, non-glass material of the inlet and the outlet are the same material. In other examples, the non-catalytic, non-glass material of the inlet and the outlet are a different material.

In another aspect, a fluid injector insert comprising an inlet and an outlet, in which the inlet comprises a substantially inert non-glass, non-stainless steel material is described.

In certain embodiments, the substantially inert non-glass, non-stainless steel material comprises titanium, aluminum, yttrium or combinations thereof. In some embodiments, the substantially inert non-glass, non-stainless steel material comprises titanium oxide, aluminum oxide, yttrium oxide or combinations thereof. In additional embodiments, the substantially inert non-glass, non-stainless steel material comprises nickel. In some embodiments, the substantially inert non-glass, non-stainless steel material can be a Hastelloy® alloy. In other embodiments, the substantially inert non-glass, non-stainless steel material comprises chromium. In additional embodiments, the substantially inert non-glass, non-stainless steel material can be an Inconel® alloy. In further embodiments, the inlet and the outlet each comprises a substantially inert non-glass, non-stainless steel material present in an effective amount to deter catalysis. In some embodiments, the substantially inert non-glass, non-stainless steel material of the inlet and the outlet are the same material. In additional embodiments, the substantially inert non-glass, non-stainless steel material of the inlet and the outlet are a different material.

In an additional aspect, a fluid injector insert comprising an inlet and an outlet, each of the inlet and the outlet comprising an internal channel coupled to each other, in which the insert is constructed and arranged to couple to an injector assembly to fluidically couple the inlet to a fluid flow path of the injector assembly, in which the inlet comprises a substantially inert metal oxide material is provided.

In certain examples, the substantially inert metal oxide material is present in a major amount. In other examples, the substantially inert metal oxide material comprises titanium, aluminum, yttrium or combinations thereof. In some examples, the substantially inert metal oxide material comprises titanium oxide, aluminum oxide, yttrium oxide or combinations thereof. In additional examples, the substantially inert metal oxide material comprises nickel or chromium.

In another aspect, a fluid injector insert comprising an inlet and an outlet, each of the inlet and the outlet comprising an internal channel coupled to each other, in which the insert is constructed and arranged to couple to an injector assembly to fluidically couple the inlet to a fluid flow path of the injector assembly, in which the inlet comprises a non-catalytic metal oxide material present in an effective amount to deter catalysis by the inlet is disclosed.

In certain embodiments, the non-catalytic metal oxide material is present in a major amount. In other embodiments, the non-catalytic metal oxide material comprises titanium, aluminum, yttrium or combinations thereof. In additional embodiments, the non-catalytic metal oxide material comprises titanium oxide, aluminum oxide, yttrium oxide or combinations thereof. In further embodiments, the non-catalytic metal oxide material comprises nickel or chromium.

In an additional aspect, a fluid injector comprising an inlet and an outlet, each of the inlet and the outlet comprising an internal channel coupled to each other, the fluid injector further comprising a fluid flow path fluidically coupled to the inlet, in which the inlet comprises a non-catalytic metal oxide material present in an major amount to deter catalysis is described.

In certain examples, the non-catalytic metal oxide material is present in a major amount. In additional examples, the non-catalytic metal oxide material comprises titanium, aluminum, yttrium or combinations thereof. In some examples, the non-catalytic metal oxide material comprises titanium oxide, aluminum oxide, yttrium oxide or combinations thereof. In other examples, the non-catalytic metal oxide material comprises nickel or chromium.

In another aspect, a fluid injector comprising an inlet and an outlet, the fluid injector further comprising a fluid flow path fluidically coupled to the inlet, in which the inlet comprises a substantially inert metal oxide material is provided.

In certain embodiments, the substantially inert metal oxide material is present in a major amount. In other embodiments, the substantially inert metal oxide material comprises titanium, aluminum, yttrium or combinations thereof. In further embodiments, the substantially inert metal oxide material comprises titanium oxide, aluminum oxide, yttrium oxide or combinations thereof. In additional embodiments, the substantially inert metal oxide material comprises nickel or chromium.

In an additional aspect, an injector assembly comprising an injector housing comprising a fluid flow path, and an injector insert mated to the injector housing, the injector insert comprising an inlet and an outlet, in which the fluid flow path of the injector housing is fluidically coupled to the inlet of the injector insert, in which the inlet comprises a substantially inert metal material is disclosed.

In certain examples, the substantially inert metal material is present in a major amount. In some examples, the substantially inert metal material comprises titanium, aluminum, yttrium or combinations thereof. In other examples, the substantially inert metal material comprises titanium oxide, aluminum oxide, yttrium oxide or combinations thereof. In additional examples, the substantially inert metal material comprises nickel or chromium.

In another aspect, an injector assembly comprising an injector housing comprising a fluid flow path, and an injector insert mated to the injector housing, the injector insert comprising an inlet and an outlet, in which the fluid flow path of the injector housing is fluidically coupled to the inlet of the injector insert, in which the inlet comprises a non-catalytic metal material present in an effective amount to deter catalysis by the inlet is described.

In certain embodiments, the non-catalytic metal material is present in a major amount. In other embodiments, the non-catalytic metal material comprises titanium, aluminum, yttrium or combinations thereof. In some embodiments, the non-catalytic metal material comprises titanium oxide, aluminum oxide, yttrium oxide or combinations thereof. In additional embodiments, the non-catalytic metal material comprises nickel or chromium.

In an additional aspect, an injector assembly comprising an injector housing comprising a fluid flow path, and an injector insert mated to the injector housing, the injector insert comprising an inlet and an outlet, in which the fluid flow path of the injector housing is fluidically coupled to the inlet of the injector insert, in which the inlet comprises a substantially inert metal oxide material is provided.

In certain examples, the substantially inert metal oxide material is present in a major amount. In additional examples, the substantially inert metal oxide material comprises titanium, aluminum, yttrium or combinations thereof. In further examples, the substantially inert metal oxide material comprises titanium oxide, aluminum oxide, yttrium oxide or combinations thereof. In some examples, the substantially inert metal oxide material comprises nickel or chromium.

In another aspect, an injector assembly comprising an injector housing comprising a fluid flow path, and an injector insert mated to the injector housing, the injector insert comprising an inlet and an outlet, in which the fluid flow path of the injector housing is fluidically coupled to the inlet of the injector insert, in which the inlet comprises a non-catalytic metal oxide material present in an major amount to deter catalysis by the inlet is disclosed.

In certain embodiments, the non-catalytic metal oxide material is present in a major amount. In other embodiments, the non-catalytic metal oxide material comprises titanium, aluminum, yttrium or combinations thereof. In additional embodiments, the non-catalytic metal oxide material comprises titanium oxide, aluminum oxide, yttrium oxide or combinations thereof. In further embodiments, the non-catalytic metal oxide material comprises nickel or chromium.

In an additional aspect, an injector assembly comprising an injector housing comprising a fluid flow path, and an injector insert mated to the injector housing, the injector insert comprising an inlet and an outlet, in which the fluid flow path of the injector housing is fluidically coupled to the inlet of the injector insert, in which the inlet comprises a non-catalytic, non-glass material present in an effective amount to deter catalysis is described.

In certain examples, the non-catalytic, non-glass material is present in a major amount. In other examples, the non-catalytic, non-glass material comprises titanium, aluminum, yttrium or combinations thereof. In some examples, the non-catalytic, non-glass material comprises titanium oxide, aluminum oxide, yttrium oxide or combinations thereof. In additional examples, the non-catalytic, non-glass material comprises nickel or chromium.

In another aspect, an injector assembly comprising an injector housing comprising a fluid flow path, and an injector insert coupled to the injector housing, the injector insert comprising an inlet and an outlet, in which the fluid flow path of the injector housing is fluidically coupled to the inlet of the injector insert, in which the insert comprises a substantially inert non-glass, non-stainless steel material is provided.

In certain embodiments, the substantially inert non-glass, non-stainless steel material is present in a major amount. In other embodiments, the substantially inert non-glass, non-stainless steel material comprises titanium, aluminum, yttrium or combinations thereof. In further embodiments, the substantially inert non-glass, non-stainless steel material comprises titanium oxide, aluminum oxide, yttrium oxide or combinations thereof. In some embodiments, the substantially inert non-glass, non-stainless steel material comprises nickel or chromium.

In an additional aspect, a kit comprising an injector insert constructed and arranged to couple to an injector assembly, the injector insert comprising an inlet and an outlet, in which the inlet comprises a substantially inert metal material is provided.

In certain examples, the kit can include the injector assembly. In other examples, the kit can include an additional injector insert constructed and arranged to couple to the injector assembly, the additional injector insert comprising an inlet and an outlet, in which the inlet of the additional injector comprises a substantially inert metal material. In some examples, the substantially inert metal material of the inlet of the additional injector insert is different than the substantially inert metal material of the inlet of the injector insert. In other examples, the kit can include a third injector insert constructed and arranged to couple to the injector assembly, the third injector insert comprising an inlet and an outlet, in which the inlet of the third injector insert comprises a substantially inert metal material.

In another aspect, a kit comprising an injector insert constructed and arranged to couple to an injector assembly, the injector insert comprising an inlet and an outlet, in which the inlet comprises a non-catalytic metal material present in an effective amount to deter catalysis by the inlet is disclosed.

In certain embodiments, the kit can include the injector assembly. In other embodiments, the kit can include an additional injector insert constructed and arranged to couple to the injector assembly, the additional injector insert comprising an inlet and an outlet, in which the inlet of the additional injector insert comprises a non-catalytic metal material present in an effective amount to deter catalysis by the inlet. In additional embodiments, the non-catalytic metal material of the inlet of the additional injector insert is different than the non-catalytic metal material of the inlet of the injector insert. In some embodiments, the kit can include a third injector insert constructed and arranged to couple to the injector assembly, the third injector insert comprising an inlet and an outlet, in which the inlet of the third injector insert comprises a non-catalytic metal material present in an effective amount to deter catalysis by the inlet of the third injector insert.

In an additional aspect, a kit comprising an injector insert constructed and arranged to couple to an injector assembly, the injector insert comprising an inlet and an outlet, in which the inlet comprises a non-catalytic, non-glass material present in an effective amount to deter catalysis by the inlet is described.

In certain examples, the kit can include the injector assembly. In other examples, the kit can include an additional injector insert constructed and arranged to couple to the injector assembly, the additional injector insert comprising an inlet and an outlet, in which the inlet of the additional injector insert comprises a non-catalytic, non-glass material present in an effective amount to deter catalysis by the inlet of the additional injector insert. In other examples, the non-catalytic, non-glass material of the inlet of the additional injector insert is different than the non-catalytic, non-glass material of the inlet of the injector insert. In some examples, the kit can include a third injector insert constructed and arranged to couple to the injector assembly, the third injector insert comprising an inlet and an outlet, in which the inlet of the third injector insert comprises a non-catalytic, non-glass material present in an effective amount to deter catalysis by the inlet of the third injector insert.

In another aspect, a kit comprising an injector insert constructed and arranged to couple to an injector assembly, the injector insert comprising an inlet and an outlet, in which the inlet comprises a substantially inert non-glass, non-stainless steel material is provided.

In certain embodiments, the kit can include the injector assembly. In other embodiments, the kit can include an additional injector insert constructed and arranged to couple to the injector assembly, the additional injector insert comprising an inlet and an outlet, in which the inlet of the additional injector insert comprises a substantially inert non-glass, non-stainless steel material. In some embodiments, the substantially inert non-glass, non-stainless steel material of the inlet of the additional injector insert is different than the substantially inert non-glass, non-stainless steel material of the inlet of the injector insert. In certain embodiments, the kit can include a third injector insert constructed and arranged to couple to the injector assembly, the third injector adapter comprising an inlet and an outlet, in which the inlet of the third injector insert comprises a substantially inert non-glass, non-stainless steel material.

In an additional aspect, a kit comprising an injector insert constructed and arranged to couple to an injector assembly, the injector insert comprising an inlet and an outlet, in which the inlet comprises a substantially inert metal oxide material is disclosed.

In certain examples, the kit can include the injector assembly. In other examples, the kit can include an additional injector insert constructed and arranged to couple to the injector assembly, the additional injector insert comprising an inlet and an outlet, in which the inlet of the additional injector insert comprises a substantially inert metal oxide material. In further examples, the substantially inert metal oxide material of the inlet of the additional injector insert is different than the substantially inert metal oxide material of the inlet of the injector insert. In some examples, the kit can include a third injector insert constructed and arranged to couple to the injector assembly, the third injector insert comprising an inlet and an outlet, in which the inlet of the third injector insert comprises a substantially inert metal oxide material.

In another aspect, a kit comprising an injector insert constructed and arranged to couple to an injector assembly, the injector insert comprising an inlet and an outlet, in which the inlet comprises a non-catalytic metal oxide material present in an effective amount to deter catalysis by the inlet is provided.

In certain embodiments, the kit can include the injector assembly. In further embodiments, the kit can include an additional injector insert constructed and arranged to couple to the injector assembly, the additional injector insert comprising an inlet and an outlet, in which the inlet of the additional injector insert comprises a non-catalytic metal oxide material present in an effective amount to deter catalysis by the inlet of the additional injector insert. In some embodiments, the non-catalytic metal oxide material of the inlet of the additional injector insert is different than the non-catalytic metal oxide material of the inlet of the injector insert. In other embodiments, the kit can include a third injector insert constructed and arranged to couple to the injector assembly, the third injector insert comprising an inlet and an outlet, in which the inlet of the third injector insert comprises a non-catalytic metal oxide material present in an effective amount to deter catalysis by the inlet of the third injector insert.

Additional features, aspect, examples and embodiments are described in more detail below.

BRIEF DESCRIPTION OF THE FIGURES

Certain embodiments are described with reference to the figures in which:

FIG. 11 is a table showing test results for 2,4-dinitrophenol using a stainless steel insert, a gold-plated insert, a titanium insert and a polished titanium insert where the ring refers to a graphite seal, in accordance with certain examples.

Figure 1:
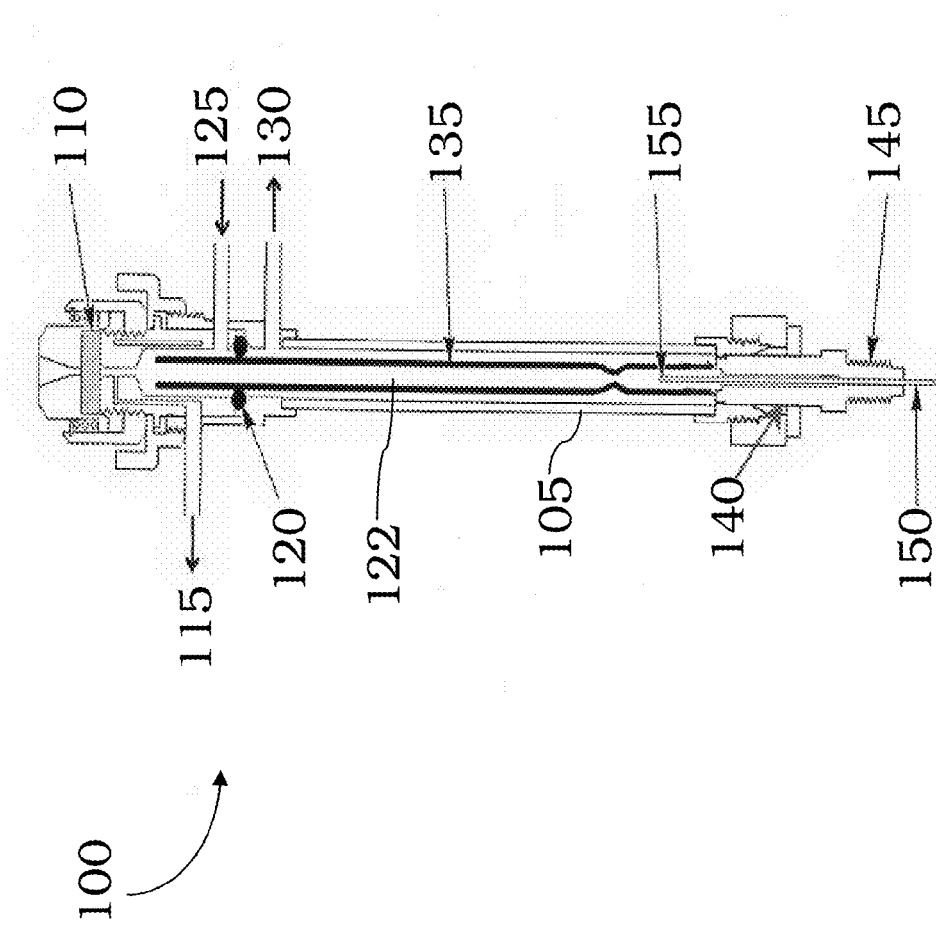
FIG. 1 is a cross-section of an injector assembly insert, in accordance with certain examples.

It will be recognized by the person of ordinary skill in the art, given the benefit of this disclosure, that certain dimensions or features in the figures may have been enlarged, distorted or shown in an otherwise unconventional or non-proportional manner to provide a more user friendly version of the figures. Where dimensions are specified in the description below, the dimensions are provided for illustrative purposes only.

DETAILED DESCRIPTION

Certain examples described herein are directed to injector inserts and injectors that include one or more materials that can render at least some portion of the injector insert or injector substantially inert or non-catalytic. The term "insert" is used herein in certain instances and is not intended to imply that the entire device or even any portion of the device need actually be inserted into another device. In some examples, a portion of an insert can couple to another device such as, for example, an injector assembly housing, and some portion of the insert may be inserted into the housing or the entire insert can be adjacent to but not actually inserted into the housing. The term "insert" is intended to be interchangeable with the term "adapter." One advantage of the inserts described herein is that different inserts can be selected and used with a single injector housing assembly. Depending on the species to be analyzed, the entire injector assembly need not be changed but instead a desired insert can be used to mitigate any unwanted effects that might result from using just the injector assembly by itself without any insert. For example, an injector insert designed to couple to an injector assembly can include a substantially inert material on a top surface that is exposed to a sample fluid flow in an injector assembly. By including the substantially inert material on surfaces that are exposed to sample, the sample that contacts or resides near the surface does not react with the surfaces to any substantial degree, and unwanted reactions are not catalyzed by the surface in any appreciable amounts. As described in more detail below, the particular type and amount of material on or in the surface can vary, and different types of materials may be desirably present to render the surface substantially inert.

In certain embodiments, the entire injector insert, if desired, can be produced from the substantially inert or non-catalytic materials. As described in more detail below, substantially inert materials are those materials that do not react with, catalyze or are otherwise affected by analytes in a sample stream to any substantial degree. Non-catalytic materials are materials that are not necessarily inert under all conditions, but they do not catalyze any reactions to a substantial degree under selected chromatographic conditions. For example, a non-catalytic material has suitable properties such that it does not catalyze any reaction during the time a sample is resident or exposed to the surface of the injector insert. There can be overlap of substantially inert materials and non-catalytic materials since substantially inert materials also do not catalyze reactions to any substantial degree no matter the residence time of the sample near the surface of the injector insert. Specific types and amounts of each of the materials are described in more detail below. To reduce overall cost, it may be desirable to include the substantially inert or non-catalytic materials only on surfaces or in components that are exposed to the sample, and other portions of the insert can be produced using conventional materials such as stainless steel.

In certain embodiments, illustrative types of materials that can be substantially inert and/or non-catalytic and are suitable for use in one or more components of the injector inserts (or entire injectors) include, but are not limited to, titanium, titanium oxide, yttrium, yttrium oxide, aluminum, aluminum oxide, nickel, nickel alloys, chromium, chromium alloys, nickel chromium alloys and the like. Desirable nickel alloys include, but are not limited to, a Hastelloy® A alloy, a Hastelloy® B alloy, a Hastelloy® B2 alloy, a Hastelloy® B3 alloy, a Hastelloy® B142T alloy, a Hastelloy® Hybrid-BC1 alloy, a Hastelloy® C alloy, a Hastelloy® C4 alloy, a Hastelloy® C22 alloy, a Hastelloy® C22HS alloy, a Hastelloy® C2000 alloy, a Hastelloy® C263 alloy, a Hastelloy® C276 alloy, a Hastelloy® D alloy, a Hastelloy® G alloy, a Hastelloy® G2 alloy, a Hastelloy® G3 alloy, a Hastelloy® G30 alloy, a Hastelloy® G50 alloy, a Hastelloy® H9M alloy, a Hastelloy® N alloy, a Hastelloy® R235 alloy, a Hastelloy® S alloy, a Hastelloy® W alloy, a Hastelloy® X alloy and other Hastelloy® alloys commercially available from Haynes International, Inc. (Kokomo, Ind.). In some examples, the substantially inert material or the non-catalytic material can be a nickel-chromium alloy such as an Inconel® 600 alloy, an Inconel® 625 alloy, an Inconel® 718 alloy or other Inconel® alloys commercially available from Special Metals Corporation (New Hartford, N.Y.). Combinations of these various materials can also be used. One or more of these materials can be present on a surface of the insert such that exposure of the sample to the surface does not result in any unwanted chemical reactions.

While certain embodiments below are described in reference to injector inserts, the components of the injector insert could be used instead in a fluid injector. For example, a fluid flow path in an entire fluid injector or fluid injector assembly can include a substantially inert or non-catalytic material to render the fluid flow paths of those devices substantially non-reactive with a sample introduced into them. Alternatively, the fluid injector can include an integrated inlet that includes one or more substantially inert materials or non-catalytic materials. It will be within the ability of the person of ordinary skill in the art, given the benefit of this disclosure, to use the materials described herein in both fluid injector inserts and fluid injectors.

In certain examples, the injector inserts described herein can be used with split or split-less injector assemblies, can be used with conventional chromatography injectors, capillary injectors or other types of injectors. In addition, the injector insert can be used in many different types of fluid chromatography including gas chromatography and liquid chromatography. For illustration purposes only, one injector assembly is shown in FIG. 1. The injector 100 includes a housing 105, a septum 110, a septum purge 115, an O-ring 120, a carrier gas inlet 125, an outlet 130, a liner 135, an injector insert 140, and a fitting 145. The injector 100 can couple to a column 150 that includes a tip 155. The insert 140 can be any of the insert described herein. In use of the injector 100, a sample is introduced through the septum 110 using a needle or other suitable device. A carrier gas entering inlet 125 can entrain the sample and carry some portion to the column 150. The column 150 is typically in a heated oven. The insert 140 is also typically heated. A top surface of the insert 140 is fluidically coupled to a fluid flow path 122 of the injector 100 such that some portion of the insert 140 is exposed to the sample in the injector 100.

In certain embodiments, exposure of the heated insert to certain compounds can result in unwanted side reactions. For example, labile compounds such as conjugated phenols and phosphorous pesticides, e.g., 2-4 dinitrophenol, methamidophos, etc., exhibit losses during introduction into a gas chromatography (GC) system. This loss is exacerbated with the use of volatile solvents such as dichloromethane. The problem can be severe when a hot, split-less injection technique is used for low level applications. A portion of the loss in the injection of labile compounds can be attributed to interaction and reactions with hot stainless steel surfaces within the injector port. Many industrial metals have catalytic affects when hot. One observable result of the losses during injection is a non-linear response across a concentration range. This issue may result in dissatisfaction of the end user if their application includes trace level detection of labile compounds, and they desire to use a volatile solvent coupled with hot split-less injections in a capillary injector assembly.

In certain embodiments, the inlet of injector inserts described herein can include one or more substantially inert metal materials. The term "inlet" is used herein to refer to the top surfaces of the injector insert and is typically the portion of the insert that is exposed to the sample. As described in more detail below, the injector insert can also include an outlet that is coupled to or integral with the inlet of the insert. The outlet is typically coupled to another component that couples to the oven of the system. In some examples, the inlet may be produced entirely from the substantially inert metal material or may include a sufficient amount of the metal material to render the inlet substantially inert. For example, the inlet can include a major amount, e.g., greater than 50% by weight, of the substantially inert metal material and can also include other inert materials. The substantially inert material can be coated to a desired thickness on the inlet or the inlet can be produced from the substantially inert material to minimize the chance any coating may flake off or leach off and interfere with the analysis. In certain embodiments, the substantially inert material or the non-catalytic material can be present in a non-coated form, e.g., no coating is present.

In certain examples, during operation of the chromatography system, the substantially inert metal material of the inlet may remain in its deposited form or may oxidize to another substantially inert metal material, e.g., a substantially inert metal oxide material. For example, the inlet of the insert can be produced using titanium and, during operation the system, the inlet can be heated to a desired temperature. Heating of the inlet can produce oxide formation in or on the inlet. For example, where titanium is used in the inlet, the titanium can be oxidized to titania (titanium oxide). Alternatively and if desired, the titanium inlet can be oxidized to titania (titanium oxide) prior to use. For example, the inlet can be sintered under non-oxidizing conditions to maintain the metal as deposited, whereas in other examples the inlet can be sintered under oxidizing conditions, e.g., in an atmosphere including oxygen, to promote oxide formation in or on the inlet.

In other examples, the inlet can include a non-catalytic material. In contrast to a substantially inert material, the non-catalytic material may be less inert and may react with certain species under certain conditions. The non-catalytic material desirably does not catalyze any reactions under the chromatographic conditions that are used. Even though the non-catalytic material may not be substantially inert under all conditions, it will not catalyze any reaction between analytes in the sample stream in the selected chromatographic conditions. The non-catalytic metal material is typically present in an effective amount to deter catalysis of any chemical reactions of species in the sample stream. In some examples, the non-catalytic metal material can be present in a major amount, e.g., 50% or more by weight, in the inlet of the injector insert. It may be desirable to use a non-catalytic material where a user knows that none of the species in the analyte stream will react or be catalyzed. The use of a non-catalytic material may also reduce costs by permitting the use of cheaper materials in the inlet of the insert.

Figure 2:
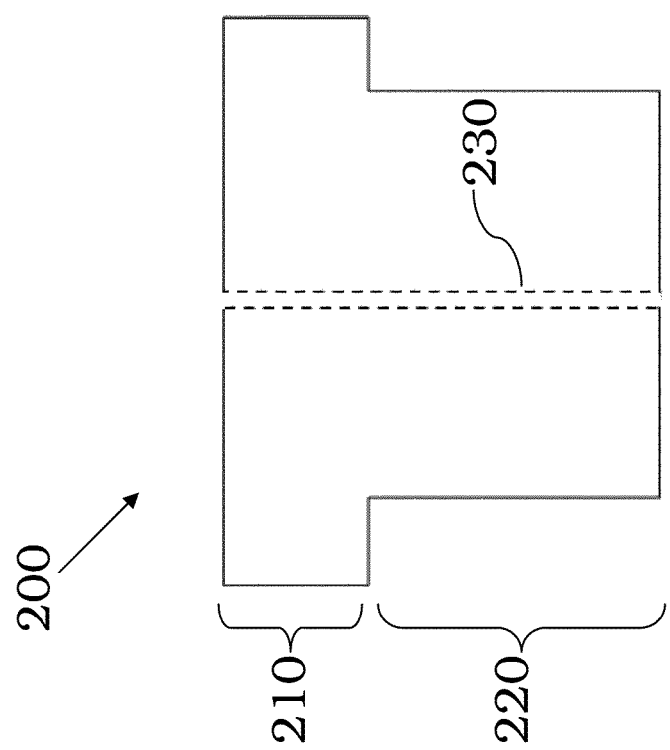
FIG. 2 is a cross-section of an injector insert, in accordance with certain examples.

In certain embodiments, a cross-section of an injector insert is shown schematically in FIG. 2. The injector insert 200, also referred to in certain instances herein as an injector adapter, includes an inlet 210 and an outlet 230. The insert 200 can also include a channel 230 that runs from the top surface of the inlet 210 to a bottom surface of the outlet 220. The channel can be sized and arranged to receive a capillary column, for example. At least some portion of the inlet 210 can be fluidically coupled to a fluid flow path in the injector assembly. As used herein, "fluidic coupling" or "fluidically coupled" refers to two or more components being connected in a suitable manner to permit fluid flow, e.g., gas flow or liquid flow, between those two components.

Figure 3:
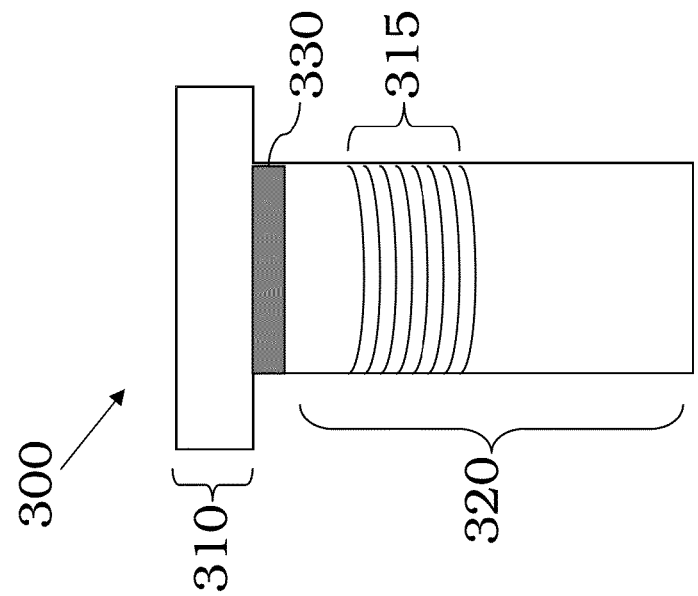
FIG. 3 is a cross-section of an injector insert in which the inlet comprises external threads to couple to the outlet, in accordance with certain examples.

In the embodiment shown in FIG. 2, the inlet and the outlet are integral such that no joints or fittings are present. In other embodiments, the inlet can be a separate component that can couple to the outlet using one or more fittings or mating threads. Such an embodiment is shown in FIG. 3. The insert 300 includes an inlet 310 comprising external threads 315. The external threads 315 can couple to internal threads on the outlet 320. It may be desirable to use, have or include a fluid tight seal 330 between the different components to reduce the likelihood that sample may escape at the junction. For example, a gasket, an adhesive or the like can be included at the interface of the inlet 310 and the outlet 320 to reduce the likelihood that sample may escape from the system. In certain embodiments, the inlet 210 or 310 may include a substantially inert material or a non-catalytic material. As sample is introduced into a chromatography system, it is exposed to the inlet 210 or 310. By including the substantially inert material or the non-catalytic material in the inlet, unwanted reactions of analyte in the sample with the fluid flow path surfaces should not occur to a substantial degree. In addition, the injector insert can be easily removed and cleaned prior to introduction of another sample. For example, the insert can be removed and washed with a suitable buffer or solvent to remove any residue from the insert that might lead to contamination of successive analyses. In addition, by using substantially inert and/or non-catalytic materials in certain embodiments, abrasive cleaning of the inlet can be performed without any substantial damage to the inlet surface.

Figure 5:
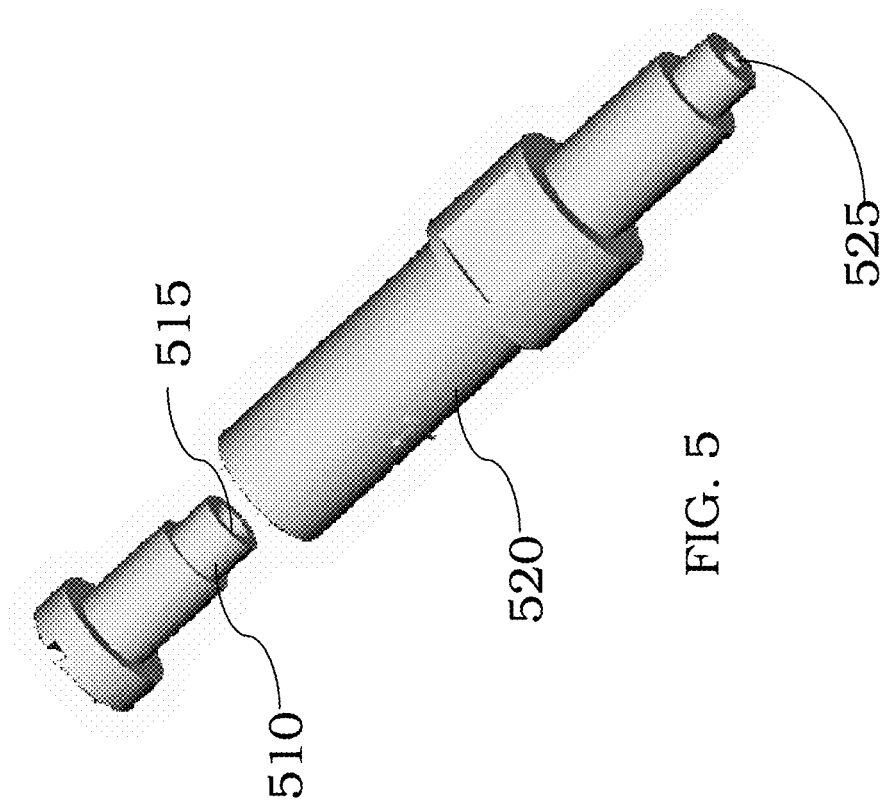
FIG. 5 is an exploded view of an inlet and an outlet of an injector insert, in accordance with certain examples.
Figure 4:
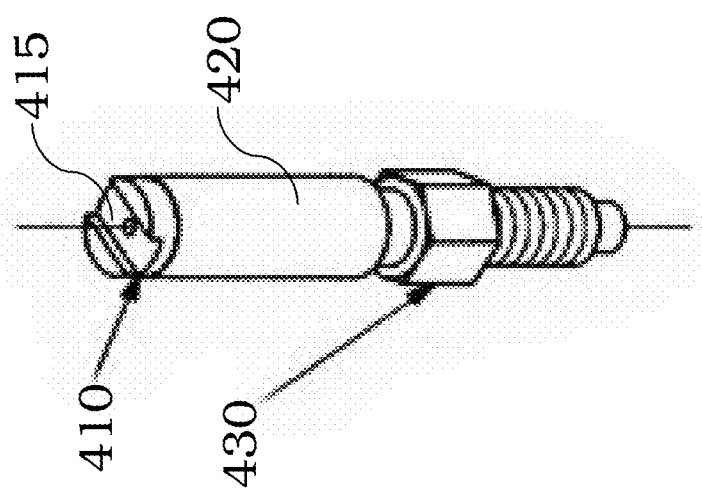
FIG. 4 is a schematic of an injector insert, in accordance with certain examples.

In certain embodiments, the body of the insert can include a slot in a top surface. In examples where a slot is present, the insert can be used for split mode operation, e.g., can provide a fluid path for splitting the sample flow. Without being bound by any particular theory, the use of a narrower slot (as compared to the width of a conventional slot) can provide increased resistance to gas flow at the insert. This resistance can assist in increasing the sample vapor in the flow path of the injector (and away from the insert) during injection and provide better recoveries. Referring to FIG. 4, an insert includes an inlet 410 having a slot 415 on a top surface, and an outlet 420. The outlet 420 is coupled to a fitting 430 that can be used to couple to a chromatography column (not shown). if desired, the fitting 430 can be omitted and the outlet 420 can be directly coupled to the chromatography column. As described herein, the inlet 410 can include a substantially inert material or a non-catalytic material to prevent or reduce the likelihood of reactions with the inlet 410. A separated view of the components are shown in FIG. 5. The inlet 510 is configured to couple to the outlet 520 either through a friction fit, using threads or using other mechanisms to securely retain the inlet 510 to the outlet 520. In some examples, a gasket can be placed between the inlet 510 and the outlet 520 to provide a fluid tight seal between the two components. The inlet 510 includes channel 510 that becomes coupled to a channel 525 in the outlet 520. The channels 515 and 525 can be configured to receive a column such that the column inlet is positioned above a top surface of the inlet 510.

Figure 7:
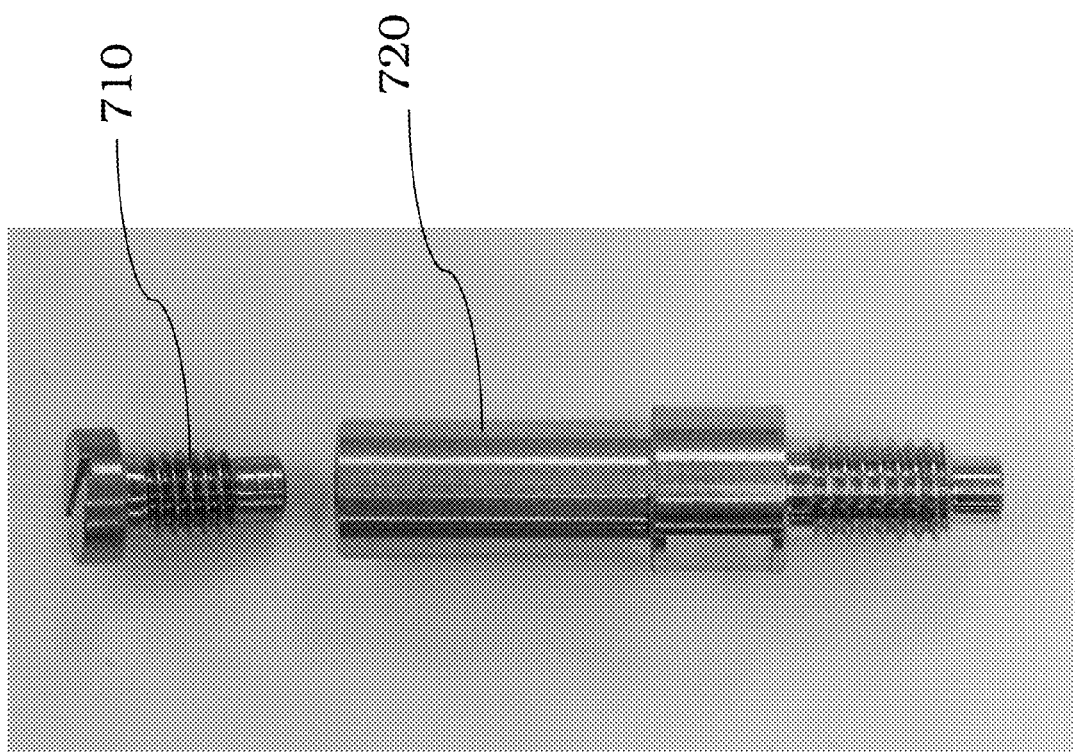
FIG. 7 is a photograph showing the injector insert used in certain measurements, in accordance with certain examples.

In certain embodiments, the inlet can have a generally cylindrical shape that may include a head portion and a body (see, for example, the photograph in FIG. 7). The head portion of the inlet can have an outer diameter of about 4 mm to about 10 mm. In certain examples, if a slot is present on a top surface of the head, the slot can have a width of about 0.5 to about 1.5 mm. In some configurations, the channel in the head can have a diameter of about 0.5 to about 1.5 mm and may be contained within the slot, if present. In certain instances, the length of the head portion can vary from about 1 mm to about 3 mm, for example. In some embodiments, the body of the inlet can be about 6 mm to about 10 mm long, for example, about 7-8 mm long and may have a diameter of about 2 mm to about 5 mm, for example, about 3 mm. In other embodiments, the entire body of the inlet need not have the same diameter, and one or more portions or segments may be smaller or greater. For example, the body of the inlet may include threads at one end to mate to the outlet, and the diameter of the threaded segment can be less than the diameter of non-threaded segments. In some examples, the outlet of the insert can mate to the inlet, as described herein, and can have a diameter of about 5 mm to about 10 mm, for example, about 6-8 mm. Similar to the inlet, in some configurations the entire outlet need not have the same diameter. In certain examples, the length of the outlet can also vary and may be, for example, about 20 mm to about 50 mm, for example, about 25-35 mm. It will be recognized by the person of ordinary skill in the art, given the benefit of this disclosure, that the size of the outlet can be adjusted to accommodate the inlet if the inlet size is increased or enlarged.

In certain examples, the outlet of the insert is typically produced using stainless steel, glasses or other materials that can withstand high temperatures, but it can be produced, if desired, from the same materials used to produce the inlet. In some examples, the outlet can be produced as a separate component that engages the inlet and held in place using a high temperature adhesive, a weld, or the like. If desired, the outlet can be formed or molded around a rod of substantially inert or non-catalytic material that can be machined into an inlet. In an alternative configuration, the entire insert may be formed from a substantially inert material or a non-catalytic material, and the channel (and optionally a slot if present) in the insert can be machined, drilled, etched or otherwise produced in the insert, e.g., the inlet can be machined from a titanium block to provide a desired shape and a channel can be drilled to provide a path for a column to be received. The channel in the insert need not be linear and may, if desired, be curved or may turn at one or more angles. It will be within the ability of the person of ordinary skill in the art, given the benefit of this disclosure, to produce the inserts described herein.

In certain embodiments, the injector inserts described herein can be used in combination with injector assemblies used in gas chromatography systems such as, for example, injector assemblies used in GC Series 400/500/600 gas chromatography systems commercially available from PerkinElmer Health Sciences, Inc. (Waltham, Mass.). In certain embodiments, the inserts can be used in a GC-mass spectrometer system such as, for example, the Clarus line of GC-MS systems commercially available from PerkinElmer Health Sciences, Inc. The insert can also be used in other types of fluid chromatography systems such as, for example, supercritical fluid chromatography systems.

Figure 6:
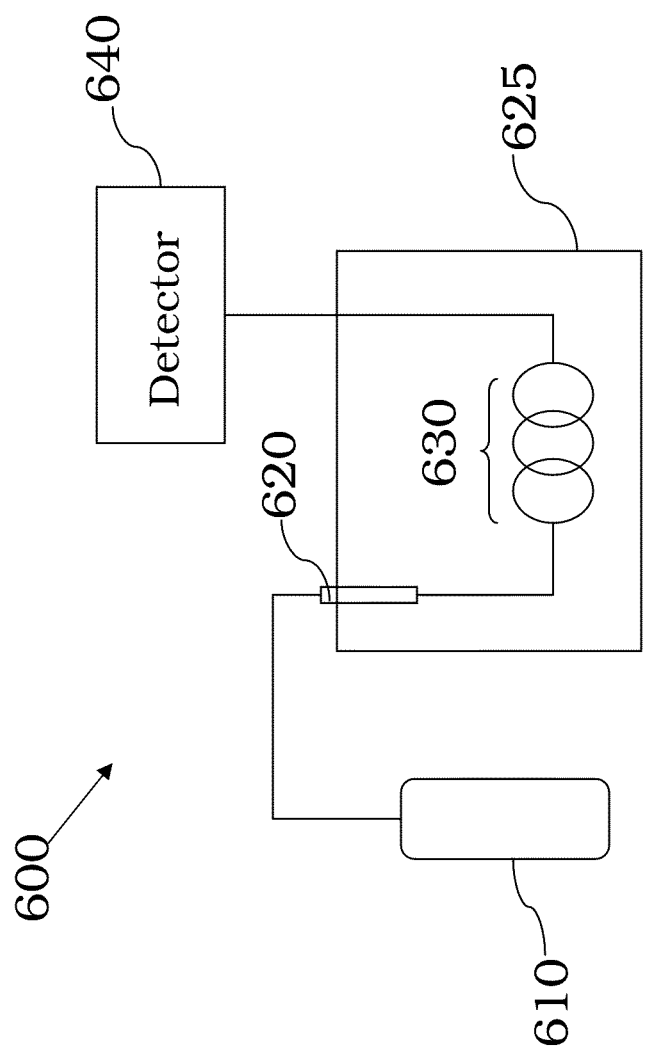
FIG. 6 is a schematic of a gas chromatography system, in accordance with certain examples.

In certain examples, an illustrative gas chromatography system is shown in FIG. 6. The system 600 includes a carrier gas supply 610 fluidically coupled to an injector 620. The injector 620 can include an insert as described herein or be configured to receive an insert as described herein. The injector 620 is fluidically coupled to a column 630, which includes a stationary phase selected to separate the analytes in a sample. The injector 620 is typically coupled to the column 630 through an injector insert and one or more ferrules or fittings to provide a fluid tight seal between the injector 620 and the column 630. The column 630 can take various forms and configurations including packed columns and open tubular or capillary columns. The column 630 is housed in an oven 625, which is configured to implement one or more temperature profiles during the separation run. The column 630 is also fluidically coupled to a detector 640. As analyte species elute from the column 630, the species are provided to the detector 640. The detector 640 can take various forms including, but not limited to a flame ionization detector, a thermal conductivity detector, a thermionic detector, an electron capture detector, an atomic emission detector, a flame photometric detector, a photoionization detector or a mass spectrometer. Where the detector takes the form of a mass spectrometer, a single mass spectrometer can be present or multiple mass spectrometers can be present.

In use of the system 600 shown in FIG. 6, a user can select the desired injector insert to be coupled to the injector 620. For example, the inlet of the insert can be fluidically coupled to a fluid flow path of the injector 620, and the column 630 can be inserted into the insert through a channel such that the column becomes fluidically coupled to the fluid flow path of the injector 620. After insertion of the injector insert, the temperature of the oven 625 may be raised to a starting temperature to permit the column 630 to warm up to that temperature. A sample can be injected through the injector 620 having the insert. Carrier gas from the gas source 610 will sweep the sample into the fluid flow path of the injector 620 where it will be exposed to the insert. Sample will also enter the column 630 where it will be separated into individual analytes. These separated analytes will elute from the column 630 and be provided to the detector 640 for detection. In between runs (or at a desired interval), the user can remove the injector insert and clean it to remove any residue prior to the next injection. Alternatively, the user can swap the installed injector insert with a different injector insert prior to the introduction of the next sample. While not shown, the system 600 may include autosamplers to permit automated operation of the system. If desired, the injector insert can be integrated into the autosampler such that the insert is automatically exchanged for a new, clean insert after a selected number of samples have been injected.

In certain embodiments, the inlet of the injector insert can include a substantially inert metal material, e.g., a material that is substantially non-reactive. In some examples, the substantially inert metal material is present in a major amount, e.g., greater than 50% by weight. In certain examples, the substantially inert metal material may include titanium, yttrium, aluminum, nickel, chromium, a nickel alloy, a chromium alloy, a nickel chromium alloy, Hastelloy® alloys, Inconel® alloys, combinations thereof, or other suitable materials. As discussed herein, the substantially inert material may take the form of a metal oxide such as, for example, titanium oxide, yttrium oxide or aluminum oxide. It may be desirable to include both titanium oxide and the cheaper aluminum oxide to reduce the overall cost of the insert. For example, the inlet may include a major amount of aluminum oxide and a minor amount of yttrium oxide or titanium oxide or both, e.g., less than 50% by weight, to render it substantially inert while at the same time reducing overall production costs. In certain embodiments, the inlet and the outlet each comprises a substantially inert metal material, e.g., each may be produced using the substantially inert material. In some examples, the substantially inert material of the different portions may be the same, whereas in other examples the substantially inert material of the different portions may be different.

In certain examples, the inlet of the insert can include a non-catalytic material present in an effective amount to deter catalysis by the inlet of the insert. The non-catalytic material may not be entirely inert, but is generally non-catalytically active under the chromatographic conditions used. Similar to the inert materials, the non-catalytic material may include a metal that is one or more of titanium, yttrium, aluminum, nickel, chromium, a nickel alloy, a chromium alloy, a nickel chromium alloy, Hastelloy® alloys, Inconel® alloys, combinations thereof, or other materials. The non-catalytic metal material may take the form of an oxide such as, for example, titanium oxide, yttrium oxide, aluminum oxide or combinations thereof. It may be desirable to include both titanium oxide and the cheaper aluminum oxide to reduce the overall cost of the insert. For example, the inlet may include a major amount of aluminum oxide and a minor amount of yttrium oxide, titanium oxide or both, e.g., less than 50% by weight, to increase the overall resistance to catalysis while reducing overall production cost. In some examples, the inlet and the outlet each comprises a non-catalytic metal material, which may be the same or may be different.

In certain embodiments, a fluid injector can be produced using the materials described herein. In particular, the substantially inert materials can be used to provide an entire injector, which permits use of the injector without the need to use an injector insert. For example, the injector can include an inlet, fluid flow path and/or outlet comprising a non-catalytic metal material present in an major amount to deter catalysis. Alternatively, the injector can include an inlet, fluid flow path or outlet comprising a major amount of a substantially inert metal material. The substantially inert metal material and the non-catalytic metal material may each be or may include titanium, yttrium, aluminum, nickel, chromium, a nickel alloy, a chromium alloy, a nickel chromium alloy, Hastelloy® alloys, Inconel® alloys, combinations thereof, or other suitable materials. Where the materials take the form of an oxide, the metal oxide may be titanium oxide, yttrium oxide, aluminum oxide or combinations thereof. Different portions of the injector may be produced using the same materials that are present in the fluid flow path or using different materials than those present in the fluid flow path. It will be within the ability of the person of ordinary skill in the art, given the benefit of this disclosure, to design injectors that include substantially inert metal materials and/or non-catalytic metal materials.

In certain embodiments, the inlet of the injector inserts (or the injectors) can include a non-catalytic, non-glass material present in an effective amount to deter catalysis by the inlet. The use of non-glass materials can provide advantages including the ability to abrasively clean the surfaces without scratching or damage as is commonly encountered with glass materials. In some examples, the non-catalytic, non-glass material can include titanium, yttrium, aluminum, nickel, chromium, a nickel alloy, a chromium alloy, a nickel chromium alloy, Hastelloy® alloys, Inconel® alloys, combinations thereof, or other suitable materials. In some examples, the inlet and the outlet may be produced from the same or different materials.

In certain embodiments, the inlet of the injector inserts (or the injectors) can include a substantially inert non-glass, non-stainless steel material. In addition to the drawbacks noted above with glass materials, stainless steel materials can catalyze unwanted reactions at the temperatures commonly used in gas chromatography. In some examples, the substantially inert non-glass, non-stainless steel material can include titanium, yttrium, aluminum, nickel, chromium, a nickel alloy, a chromium alloy, a nickel chromium alloy, Hastelloy® alloys, Inconel® alloys, combinations thereof, or other suitable materials. In some examples, the inlet and the outlet may be produced from the same or different materials.

In certain embodiments, the fluid injector insert can be constructed and arranged to couple to an injector assembly to fluidically couple the inlet of the insert to a fluid flow path of the injector assembly, in which the inlet of the insert comprises a substantially inert metal oxide material. For example, the substantially inert metal oxide material can be present in a major amount. In some examples, the substantially inert metal oxide material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In other embodiments, the fluid injector insert can be constructed and arranged to couple to an injector assembly to fluidically couple the inlet of the insert to a fluid flow path of the injector assembly, in which the inlet of the insert comprises a non-catalytic metal oxide material present in an effective amount to deter catalysis in the fluid flow path of the insert. In some examples, the non-catalytic metal oxide can be present in a major amount. In other examples, the non-catalytic metal oxide material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In additional examples, an injector assembly comprising an injector housing comprising a fluid flow path can be used. The assembly can also include an injector insert coupled to the inlet of the injector housing, the injector insert comprising an inlet and an outlet, in which the fluid flow path of the injector housing is fluidically coupled to the inlet, and in which the inlet comprises a substantially inert metal material. In some examples, the substantially inert metal material is present in a major amount. In certain examples, the substantially inert metal material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In other examples, an injector assembly can include an injector insert coupled to an injector housing, the injector insert comprising an inlet and an outlet, in which a fluid flow path of the injector housing is fluidically coupled to the inlet, and in which the inlet comprises a non-catalytic metal material present in an effective amount to deter catalysis in the fluid flow path of the insert. In some examples, the non-catalytic metal material is present in a major amount. In certain examples, the non-catalytic metal material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In certain embodiments, an injector assembly can include an injector insert coupled to an injector housing, the injector insert comprising an inlet and an outlet, in which the fluid flow path of the injector insert is fluidically coupled to the inlet, and in which the inlet comprises a substantially inert metal oxide material. In some examples, the substantially inert metal oxide material is present in a major amount. In certain examples, the substantially inert metal oxide material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In certain embodiments, an injector assembly can include an injector insert coupled to an injector housing, the injector insert comprising an inlet and an outlet, in which a fluid flow path of the injector housing is fluidically coupled to the inlet, and in which the inlet comprises a non-catalytic metal oxide material present in an major amount to deter catalysis by the inlet. In some examples, the non-catalytic metal oxide material is present in a major amount. In certain examples, the non-catalytic metal oxide material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In other embodiments, the injector assembly can include an injector insert coupled to an injector housing, the injector insert comprising an inlet and an outlet, in which a fluid flow path of the injector insert is fluidically coupled to the inlet, and in which the inlet comprises a non-catalytic, non-glass material present in an effective amount to deter catalysis by the inlet. In some examples, the non-catalytic, non-glass material is present in a major amount. In certain examples, the non-catalytic, non-glass material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In other examples, the injector assembly can include an injector insert coupled to an injector housing, the injector insert comprising an inlet and an outlet, in which a fluid flow path of the injector housing is fluidically coupled to the inlet, and in which the inlet comprises a substantially inert non-glass, non-stainless steel material. In some examples, the substantially inert non-glass, non-stainless steel material is present in a major amount. In certain examples, the substantially inert non-glass, non-stainless steel material can comprise titanium, yttrium, aluminum, nickel, chromium, a nickel alloy, a chromium alloy, a nickel chromium alloy, Hastelloy® alloys, Inconel® alloys, combinations thereof, or other suitable materials.

In certain embodiments, the injector insert can be included in a kit. For example, the kit can include an injector insert comprising an inlet and an outlet, in which the inlet comprises a substantially inert metal material. In some examples, the kit can include an injector assembly. In other examples, the kit can include an additional injector insert constructed and arranged to couple to the injector assembly, the additional injector insert comprising an inlet and an outlet, in which the inlet of the additional injector insert comprises a substantially inert metal material. In some examples, the substantially inert metal material of the inlet of the additional injector insert is different than the substantially inert metal material of the inlet of the injector insert. In additional examples, the kit can include a third injector insert constructed and arranged to couple to the injector assembly, the third injector insert comprising an inlet and an outlet, in which the inlet of the third injector insert comprises a substantially inert metal material.

In other embodiments, a kit can include an injector insert constructed and arranged to couple to an injector assembly, the injector insert comprising an inlet and an outlet, in which the inlet comprises a non-catalytic metal material present in an effective amount to deter catalysis by the inlet. In some embodiments, the kit can include an injector assembly. In further embodiments, the kit can include an additional injector insert constructed and arranged to couple to the injector assembly, the additional injector insert comprising an inlet and an outlet, in which the inlet comprises a non-catalytic metal material present in an effective amount to deter catalysis by the inlet of the additional injector insert. In some examples, the non-catalytic metal material of the inlet of the additional injector insert is different than the non-catalytic metal material of the inlet of the injector insert. In other examples, the kit can include a third injector insert constructed and arranged to couple to the injector assembly, the third injector insert comprising an inlet and an outlet, in which the inlet of the third injector insert comprises a non-catalytic metal material present in an effective amount to deter catalysis by the inlet of the third injector insert.

In certain embodiments, a kit can include an injector insert constructed and arranged to couple to an injector assembly, the injector insert comprising an inlet and an outlet, in which the inlet comprises a non-catalytic, non-glass material present in an effective amount to deter catalysis by the inlet. In some examples, the kit can include an injector assembly. In other examples, the kit can include an additional injector insert constructed and arranged to couple to the injector assembly, the additional injector insert comprising an inlet and an outlet, in which the inlet of the additional injector insert comprises a non-catalytic, non-glass material present in an effective amount to deter catalysis by the inlet. In certain embodiments, the non-catalytic, non-glass material of the inlet of the additional injector insert is different than the non-catalytic, non-glass material of the inlet of the injector insert. In some examples, the kit can include a third injector insert constructed and arranged to couple to the injector assembly, the third injector insert comprising an inlet and an outlet, in which the inlet of the third injector insert comprises a non-catalytic, non-glass material present in an effective amount to deter catalysis by the inlet of the third injector insert.

In certain examples, a kit can include an injector insert constructed and arranged to couple to an injector assembly, the injector insert comprising an inlet and an outlet, in which the inlet comprises a substantially inert non-glass, non-stainless steel material. In additional examples, the kit can include the injector assembly. In some examples, the kit can include an additional injector insert constructed and arranged to couple to the injector assembly, the additional injector insert comprising an inlet and an outlet, in which the inlet of the additional injector insert comprises a substantially inert non-glass, non-stainless steel material. In certain embodiments, the substantially inert non-glass, non-stainless steel material of the inlet of the additional injector insert is different than the substantially inert non-glass, non-stainless steel material of the inlet of the injector insert. In other embodiments, the kit can include a third injector insert constructed and arranged to couple to the injector assembly, the third injector insert comprising an inlet and an outlet, in which the inlet of the third injector insert comprises a substantially inert non-glass, non-stainless steel material.

In certain embodiments, a kit can include an injector insert constructed and arranged to couple to an injector assembly, the injector insert comprising an inlet and an outlet, in which the inlet comprises a substantially inert metal oxide material. In some embodiments, the kit can include an injector assembly. In additional embodiments, the kit can include an additional injector insert constructed and arranged to couple to the injector assembly, the additional injector insert comprising an inlet and an outlet, in which the inlet of the additional injector insert comprises a substantially inert metal oxide material. In further embodiments, the substantially inert metal oxide material of the inlet of the additional injector insert is different than the substantially inert metal oxide material of the inlet of the injector insert. In other embodiments, the kit can include a third injector insert constructed and arranged to couple to the injector assembly, the third injector insert comprising an inlet and an outlet, in which the inlet of the third injector insert comprises a substantially inert metal oxide material.

In certain examples, a kit can include an injector insert constructed and arranged to couple to an injector assembly, the injector insert comprising an inlet and an outlet, in which the inlet comprises a non-catalytic metal oxide material present in an effective amount to deter catalysis by the inlet. In some examples, the kit can include an injector assembly. In additional examples, the kit can include an additional injector insert constructed and arranged to couple to the injector assembly, the additional injector insert comprising an inlet and an outlet, the inlet of the additional injector insert comprising a non-catalytic metal oxide material present in an effective amount to deter catalysis by the e inlet of the additional injector insert. In other examples, the non-catalytic metal oxide material of the inlet of the additional injector insert is different than the non-catalytic metal oxide material of the inlet of the injector insert. In further examples, the kit can include a third injector insert constructed and arranged to couple to the injector assembly, the third injector insert comprising an inlet and an outlet, in which the inlet of the third injector insert comprises a non-catalytic metal oxide material present in an effective amount to deter catalysis by the inlet of the third injector insert.

In certain embodiments, a method of facilitating chromatographic analysis of a sample is provided. In certain examples, the method comprises providing an injector insert comprising an inlet and an outlet, in which the insert is constructed and arranged to couple to an injector assembly to fluidically couple the inlet of the insert to a fluid flow path of the injector assembly, in which the inlet of the insert comprises a substantially inert metal material.

In other embodiments, a method of facilitating chromatographic analysis of a sample can include providing an injector insert comprising an inlet and an outlet, in which the insert is constructed and arranged to couple to an injector assembly to fluidically couple the inlet of the insert to a fluid flow path of the injector assembly, in which the inlet of the insert comprises a non-catalytic metal material present in an effective amount to deter catalysis by the inlet.

In additional embodiments, a method of facilitating chromatographic analysis of a sample can include providing a fluid injector comprising an inlet and an outlet, in which the inlet comprises a non-catalytic metal material present in an major amount to deter catalysis.

In other embodiments, a method of facilitating chromatographic analysis of a sample can include providing a fluid injector comprising an inlet and an outlet, in which the inlet comprises a major amount of a substantially inert metal material.

In some examples, a method of facilitating chromatographic analysis of a sample can include providing a fluid injector insert comprising an inlet and an outlet, in which the inlet comprises a non-catalytic, non-glass material present in an effective amount to deter catalysis by the inlet.

In other examples, a method of facilitating chromatographic analysis of a sample can include providing a fluid injector insert comprising an inlet and an outlet, in which the inlet comprises a substantially inert non-glass, non-stainless steel material.

In additional examples, a method of facilitating chromatographic analysis of a sample can include providing a fluid injector insert comprising an inlet and an outlet, in which the insert is constructed and arranged to couple to an injector assembly to fluidically couple the inlet of the insert to a fluid flow path of the injector assembly, in which the inlet comprises a substantially inert metal oxide material.

In other embodiments, a method of facilitating chromatographic analysis of a sample can include providing a fluid injector insert comprising an inlet and an outlet, in which the insert is constructed and arranged to couple to an injector assembly to fluidically couple the inlet of the insert to a fluid flow path of the injector assembly, in which the inlet comprises a non-catalytic metal oxide material present in an effective amount to deter catalysis by the inlet.

In additional embodiments, a method of facilitating chromatographic analysis of a sample can include providing a fluid injector comprising an inlet and an outlet, in which the inlet comprises a non-catalytic metal oxide material present in an major amount to deter catalysis.

In further embodiments, a method of facilitating chromatographic analysis of a sample can include providing a fluid injector comprising an inlet and an outlet, in which the inlet comprises a substantially inert metal oxide material.

In some embodiments, a method of facilitating chromatographic analysis of a sample can include providing an injector assembly comprising an injector housing comprising a fluid flow path, and an injector insert coupled to the injector housing, the injector insert comprising an inlet and an outlet, in which the fluid flow path the inlet of the injector insert is fluidically coupled to the fluid flow path of the injector housing, the inlet of the injector insert comprising a substantially inert metal material.

In some examples, a method of facilitating chromatographic analysis of a sample can include providing an injector assembly comprising an injector housing comprising a fluid flow path, and an injector insert coupled to the injector housing, the injector insert comprising an inlet and an outlet, in which the inlet of the injector insert is fluidically coupled to the fluid flow path of the injector housing, the inlet of the injector insert comprising a non-catalytic metal material present in an effective amount to deter catalysis by the inlet.

In other examples, a method of facilitating chromatographic analysis of a sample can include providing an injector assembly comprising an injector housing comprising a fluid flow path, and an injector insert coupled to the injector housing, the injector insert comprising an inlet and an outlet, in which the inlet of the injector insert is fluidically coupled to the fluid flow path of the injector housing, the inlet of the injector insert comprising a substantially inert metal oxide material.

In further examples, a method of facilitating chromatographic analysis of a sample can include providing an injector assembly comprising an injector housing comprising a fluid flow path, and an injector insert coupled to the injector housing, the injector insert comprising an inlet and an outlet, in which the inlet of the injector insert is fluidically coupled to the fluid flow path of the injector housing, the inlet of the injector insert comprising a non-catalytic metal oxide material present in an major amount to deter catalysis.

In some embodiments, a method of facilitating chromatographic analysis of a sample can include providing an injector assembly comprising an injector housing comprising a fluid flow path, and an injector insert coupled to the injector housing, the injector insert comprising an inlet and an outlet, in which the inlet of the injector insert is fluidically coupled to the fluid flow path of the injector housing, the inlet of the injector insert comprising a non-catalytic, non-glass material present in an effective amount to deter catalysis.

In other embodiments, a method of facilitating chromatographic analysis of a sample can include providing an injector assembly comprising an injector housing comprising a fluid flow path, and an injector insert coupled to the injector housing, the injector insert comprising an inlet and an outlet, in which the inlet of the injector insert is fluidically coupled to the fluid flow path of the injector housing, the inlet comprising a substantially inert non-glass, non-stainless steel material.

In certain embodiments of the injector inserts and injector assemblies described herein, the inlet of the injector inserts (or the injectors) can include titanium, yttrium, aluminum, nickel, chromium, a nickel alloy, a chromium alloy, a nickel chromium alloy, Hastelloy® alloys, Inconel® alloys, combinations thereof, or other materials. In some examples, the inlet and the outlet may be produced from the same or different materials.

Certain specific examples and spectra are described below to illustrate further the novel technology described herein. These examples are merely illustrative and are not intended to limit the scope of the claims appended hereto.

Example 1

Several tests were performed to evaluate an insert. Tests were performed using a Clarus 680 GC using an injector temperature of 280 degrees Celsius with a temperature ramp of 35 to 200 degrees Celsius and a Clarus 600 MS using a source temperature of 250 degrees Celsius and scanning 50-400 amu. The column that was used was an Elite 5 ms Column with dimensions of 30 m by 0.25 mm by 0.25 microns.

Referring to FIG. 7, an injector insert is shown that was used in the measurements described in this example. The insert 700 includes a titanium inlet 710 that was configured to mate to a stainless steel outlet (or body) 720.

Figure 8:
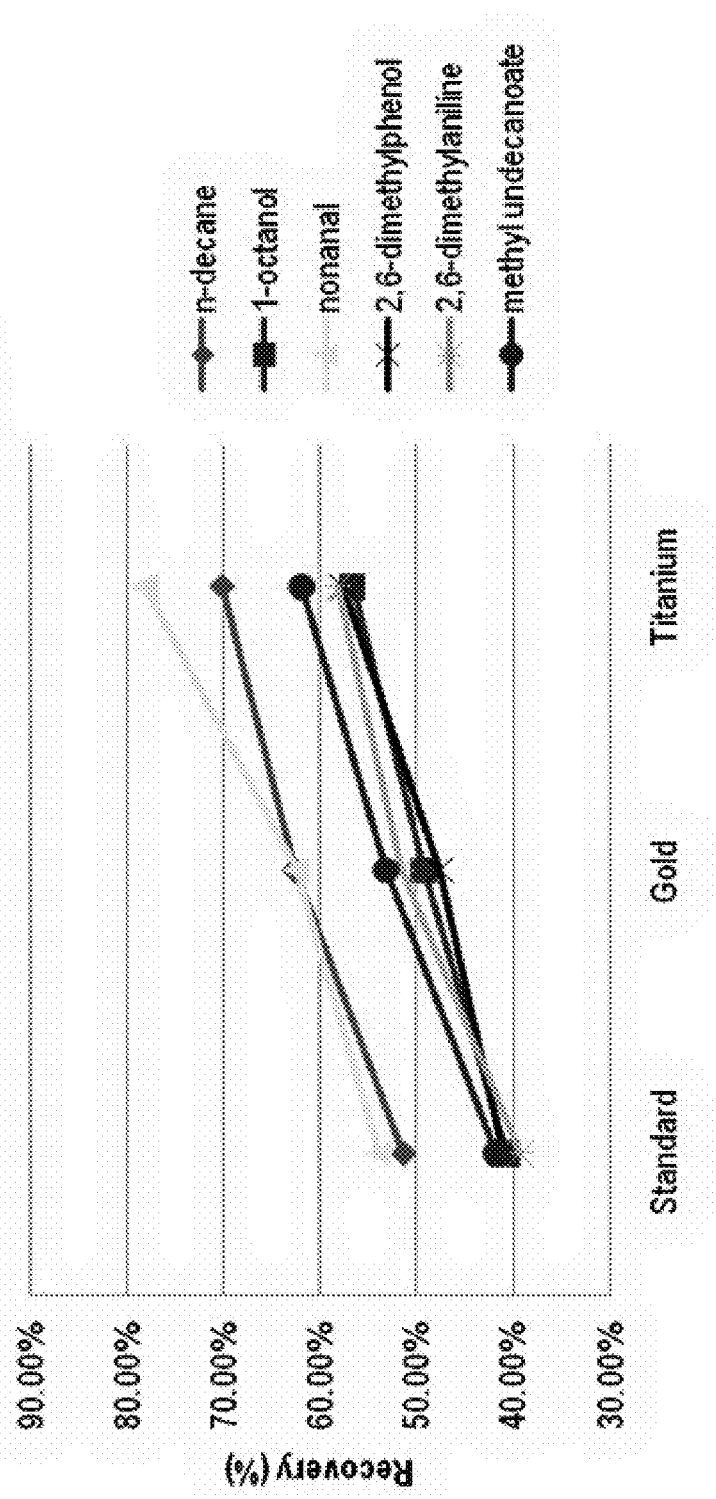
FIG. 8 is a graph showing recovery tests for a mixture of species using a standard stainless steel injector insert, a gold-plated injector insert and an insert including a titanium inlet, in accordance with certain examples.

Referring to FIG. 8, a graph is provided that shows recoveries of a series of compounds present in a commercially available Grob mix. As shown in the graph, recoveries improve when a titanium insert is used as compared to the recoveries for a stainless steel insert and a gold-plated insert.

Figure 9:
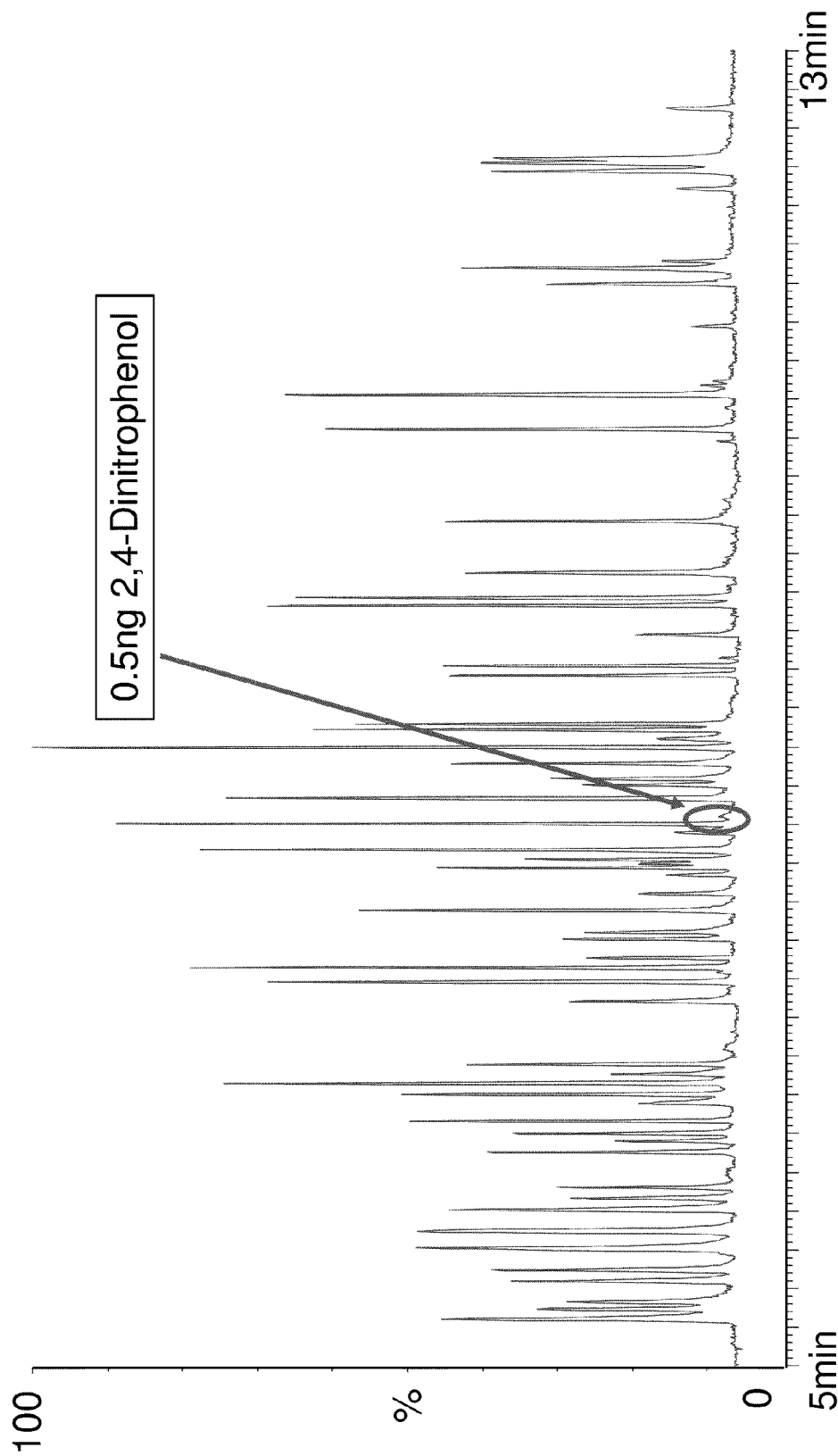
FIG. 9 shows the results of a splitless TIC chromatography measurement using a US-EPA 8270 standard mixture, in accordance with certain examples.

Referring to FIG. 9, a chromatogram from a splitless TIC chromatography run is shown for a US-EPA 8270 standard mixture. As can be seen in the chromatogram, the 2,4-dinitrophenol (DNP) peak has a low intensity compared to the other peaks in the sample, and it can be difficult to observe.

Figure 10:
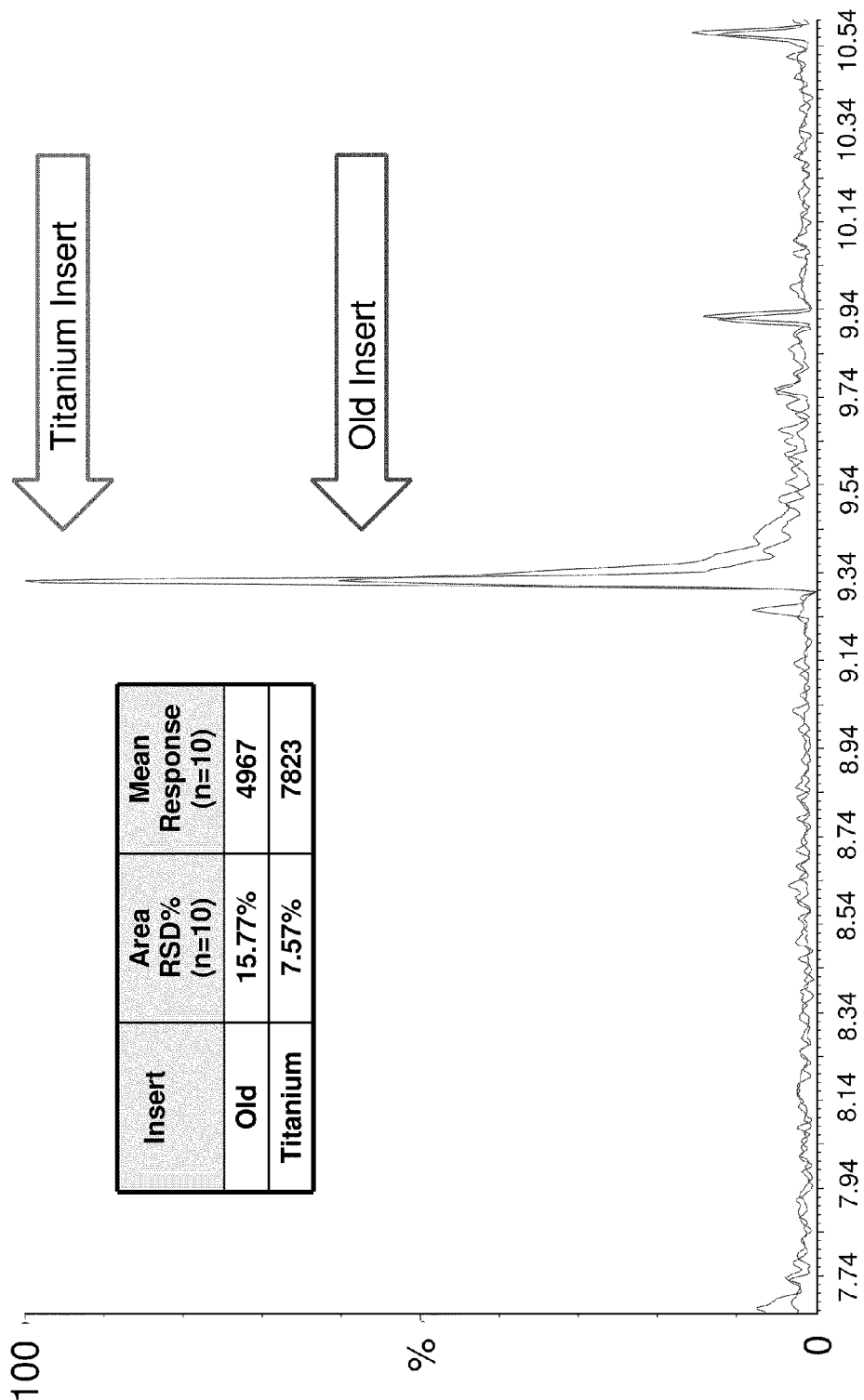
FIG. 10 shows a the recovery results of injection of 0.5 ng of 2,4-dinitrophenol using splitless TIC chromatography and a stainless steel insert and an inlet comprising a titanium insert, in accordance with certain examples.

Referring to FIG. 10, a chromatogram from a splitless TIC chromatography run for an ion having m/z 184, representative of DNP, is shown. The intensity using the titanium insert is much improved as compared to a stainless steel insert (labeled as "old insert" in FIG. 10).

Referring to FIG. 11, a table is shown demonstrating that linearity is as good or better with a titanium insert than with a standard insert when DNP was measured. The standard insert included stainless steel, and the stainless steel insert was stainless steel but also had a similar geometry (top slot width) as the titanium inserts. No response was observed at 0.5 ppm using the standard or stainless steel inserts, while suitable results were obtained when the titanium insert was used. These results are consistent with the titanium material improving linearity rather than a change in geometry of the insert improving the linearity.

When introducing elements of the examples disclosed herein, the articles "a," "an," "the" and "said" are intended to mean that there are one or more of the elements. The terms "comprising," "including" and "having" are intended to be open-ended and mean that there may be additional elements other than the listed elements. It will be recognized by the person of ordinary skill in the art, given the benefit of this disclosure, that various components of the examples can be interchanged or substituted with various components in other examples.

Although certain aspects, examples and embodiments have been described above, it will be recognized by the person of ordinary skill in the art, given the benefit of this disclosure, that additions, substitutions, modifications, and alterations of the disclosed illustrative aspects, examples and embodiments are possible.

What is claimed is:

1. A fluid injector insert comprising an injector insert inlet coupled to a separate injector insert outlet to provide a channel between the coupled injector insert inlet and the injector insert outlet, wherein the injector insert inlet is constructed and arranged to couple to an injector assembly to fluidically couple a fluid flow path of the injector insert to a fluid flow path of the injector assembly so that a top surface of the injector insert inlet will be exposed to sample in the fluid flow path of the injector assembly, wherein the top surface of the injector insert inlet comprises a substantially inert metal material that is exposed to sample in the fluid flow path of the injector assembly, and wherein the injector insert outlet and the channel are configured to receive a column to fluidically couple the received column to the injector insert inlet to provide fluidic coupling between the injector insert inlet and the column to permit sample to flow to the column.

2. The fluid injector insert of claim 1, wherein the substantially inert metal material is present on the top surface at more than 50% by weight.

3. The fluid injector insert of claim 1, wherein the substantially inert metal material comprises titanium, aluminum, yttrium or combinations thereof.

4. The fluid injector insert of claim 3, wherein the substantially inert metal material comprises titanium oxide, aluminum oxide, yttrium oxide or combinations thereof.

5. The fluid injector insert of claim 1, wherein the substantially inert metal material comprises nickel.

6. The fluid injector insert of claim 5, wherein the substantially inert metal material is a nickel alloy.

7. The fluid injector insert of claim 1, wherein the substantially inert metal material comprises chromium.

8. The fluid injector insert of claim 7, wherein the substantially inert metal material is a nickel-chromium alloy.

9. The fluid injector insert of claim 1, wherein the top surface of the inlet and the outlet each comprises a substantially inert metal material.

10. The fluid injector insert of claim 9, wherein the substantially inert metal material of the inlet and the outlet are the same material.

11. A fluid injector insert comprising an injector insert inlet coupled to a separate injector insert outlet, wherein the injector insert inlet is constructed and arranged to fluidically couple to a fluid flow path of the injector assembly so that a top surface of the injector insert inlet will be exposed to sample in the fluid flow path of the injector assembly, wherein the top surface of the injector insert inlet comprises a non-catalytic metal material present in an effective amount to deter catalysis by the top surface of the injector insert inlet that is exposed to the sample in the fluid flow path, and wherein the injector insert outlet and the channel are configured to receive a column to fluidically couple the received column to the injector insert inlet and to provide fluidic coupling between the injector insert inlet and the column to permit sample to flow to the column.

12. The fluid injector insert of claim 11, wherein the non-catalytic metal material is present on the top surface at more than 50% by weight.

13. The fluid injector insert of claim 11, wherein the non-catalytic metal material comprises titanium, aluminum, yttrium or combinations thereof.

14. The fluid injector insert of claim 13, wherein the non-catalytic metal material comprises titanium oxide, aluminum oxide, yttrium oxide or combinations thereof.

15. The fluid injector insert of claim 11, wherein the non-catalytic metal material comprises nickel.

16. The fluid injector insert of claim 15, wherein the non-catalytic metal material is a nickel alloy.

17. The fluid injector insert of claim 11, wherein the non-catalytic metal material comprises chromium.

18. The fluid injector insert of claim 17, wherein the non-catalytic metal material is a nickel-chromium alloy.

19. The fluid injector insert of claim 11, wherein the top surface of the inlet and the outlet each comprises a non-catalytic metal material.

20. The fluid injector insert of claim 19, wherein the non-catalytic metal material of the inlet and the outlet are the same material.

* * * * *